US012782367B2

(12) United States Patent
Sawamura et al.

(10) Patent No.: US 12,782,367 B2
(45) Date of Patent: Nov. 3, 2026

(54) METHOD FOR QUANTIFYING ADIPONECTIN AND ANALYTICAL REAGENT USED THEREFOR

(71) Applicant: Tatsuya Sawamura, Matsumoto (JP)

(72) Inventors: Tatsuya Sawamura, Matsumoto City (JP); Akemi Kakino, Matsumoto City (JP)

(73) Assignee: Tatsuya Sawamura, Matsumoto (JP)

( * ) Notice: Subject to any disclaimer, the term of this patent is extended or adjusted under 35 U.S.C. 154(b) by 977 days.

(21) Appl. No.: 17/909,036

(22) PCT Filed: Mar. 3, 2021

(86) PCT No.: PCT/JP2021/008063
§ 371 (c)(1),
(2) Date: Sep. 2, 2022

(87) PCT Pub. No.: WO2021/177333
PCT Pub. Date: Sep. 10, 2021

(65) Prior Publication Data

US 2023/0243855 A1 Aug. 3, 2023

(30) Foreign Application Priority Data

Mar. 3, 2020 (JP) ................................ 2020-035579

(51) Int. Cl.
*G01N 33/74* (2006.01)
*G01N 33/53* (2006.01)
*G01N 33/68* (2006.01)
*G01N 33/92* (2006.01)

(52) U.S. Cl.
CPC ............ *G01N 33/74* (2013.01); *G01N 33/53* (2013.01); *G01N 33/68* (2013.01); *G01N 33/92* (2013.01); *G01N 2800/042* (2013.01); *G01N 2800/32* (2013.01)

(58) Field of Classification Search
None
See application file for complete search history.

(56) References Cited

U.S. PATENT DOCUMENTS

2016/0195551 A1 7/2016 Maeda et al.

FOREIGN PATENT DOCUMENTS

| | | | |
|---|---|---|---|
| JP | 2006-526762 | A | 11/2006 |
| JP | 2007-519894 | A | 7/2007 |
| JP | 2013-257343 | A | 12/2013 |
| JP | 2017-131172 | A | 8/2017 |
| WO | WO 2009/078151 | A1 | 6/2009 |
| WO | WO 2013/190679 | A1 | 12/2013 |
| WO | WO 2015/033986 | A1 | 3/2015 |
| WO | WO 2017/006431 | A1 | 1/2017 |
| WO | WO 2019/159934 | A1 | 8/2019 |

OTHER PUBLICATIONS

Fukuda et al., J. Biol. Chem. (2017) 292(19) 7840-7849 (Year: 2017).*
Sasaoka et al., J Atheroscler Thromb, 2025; 32: 1109-1121 (Year: 2025).*
Pischon et al., Atherosclerosis, 2011; 219: 322-329 (Year: 2011).*
Basati et al., "Reduced plasma adiponectin levels relative to oxidized low density lipoprotein and nitric oxide in coronary adiponectin artery disease patients", *Clinics* 66(7):1129-1135 (2011).
Denzel et al., "T-cadherin is critical for adiponectin-mediated cardioprotection in mice", *The Journal of Clinical Investigation* 120(12):4342-4352 (2010).
European Search Report for EP Application No. 21764171.1, mailed Mar. 11, 2024, 14 pages.
Hug et al., "T-cadherin is a receptor for hexameric and high-molecular-weight forms of Acrp30/adiponectin", *PNAS* 101(28):10308-10313 (2004).
Parker-Duffen et al., "T-cadherin is Essential for Adiponectin-mediated Revascularization", *The Journal of Biological Chemistry* 288(34):24886-24897 (2013).
International Search Report for International Application No. PCT/JP2021/008063, mailed May 25, 2021, 6 pages.
Kakino et al., "Abstract 16832: Oxidized LDL and Adiponectin Interact and Regulate the Other's Respective Functions", *Circulation* 134(Suppl. 1):16832 (2016).
Kakino et al., "P3789—Adiponectin forms a complex with electronegative L5 LDL in human plasma and inhibits its atherogenic effects", *European Heart Journal* 39 (Supplement):800-801 (2018).
Kakino et al., "Adiponectin forms a complex with atherogenic LDL and inhibits its downstream effects", *Journal of Lipid Research* vol. 62, (2021).
Kakino et al., "P3780—Adiponectin forms a complex with electronegative L5 LDL in human plasma and inhibits its atherogenic effects", *European Heart Journal* 39 (Supplement):800-801 (2018).
Basati et al., "Reduced plasma adiponectin levels relative to oxidized low density lipoprotein and nitric oxide in coronary artery disease patients", *Clinics* 66(7):1129-1135 (2011).

* cited by examiner

*Primary Examiner* — Christina M Borgeest
(74) *Attorney, Agent, or Firm* — Lathrop GPM LLP; Brian C. Trinque; Tanya D'Souza

(57) ABSTRACT

The present invention provides a method for quantifying adiponectin including quantifying adiponectin while distinguishing between an adiponectin having physiological activity and an adiponectin having pathological activity in a quantification of adiponectin in body fluid.

4 Claims, 6 Drawing Sheets

METHOD FOR QUANTIFYING ADIPONECTIN AND ANALYTICAL REAGENT USED THEREFOR

TECHNICAL FIELD

The present invention relates to a method for quantifying adiponectin, which is a substance involved in metabolism in blood, and an analytical reagent used therefor.

BACKGROUND ART

Adiponectin is a secreted protein expressed in adipocytes and is believed to be involved in glucose regulation and fatty acid breakdown. In general, adiponectin is known as a good adipokine because the concentration of adiponectin in the blood is inversely correlated with the amount of fat in the body, and it has been attracting attention as a substance having a function of suppressing metabolic disorder syndrome (so-called metabolic syndrome), arteriosclerosis associated therewith and the like, which have been regarded as a problem in recent years.

Adiponectin is known to include monomers, trimers and hexamers obtained by polymerizing multiple monomers, and multimers obtained by further polymerizing these. The total amount of these adiponectins can be quantified using an anti-adiponectin antibody, which has been used as a quantification technique so far. On the other hand, adiponectin, which is mainly composed of multiple monomers, is considered to have physiological functions.

Patent Document 1 discloses a technique for quantifying multimeric high-molecular-weight adiponectin, which is believed to be involved in the metabolism. This technique recognizes the S-S binding site that contributes to the intermolecular binding of adiponectin or its vicinity, and aims to selectively measure high-molecular-weight adiponectin in a sandwich immunoassay system. In the sandwich immunoassay system, antibodies that specifically recognize high-molecular-weight adiponectin are used as primary and secondary antibodies.

CITATION LIST

Patent Document

[Patent Document 1] PCT International Publication No. WO 2009/078151

SUMMARY OF INVENTION

Technical Problem

However, while adiponectin is believed to contribute to the metabolism of fats and sugars, a high blood adiponectin concentration may rather increase the risk of diseases related to these metabolisms. For example, the risk of cardiovascular disease is rather increased with high blood levels of adiponectin.

Therefore, it is not possible to fully understand the physiological activity of adiponectin and its influence on the above-mentioned diseases only by quantifying the total amount of adiponectin, or the amounts of adiponectins having structures such as a monomer or multimer.

Here, for example, in the case of high-density lipoprotein (HDL protein) known as good cholesterol, dysfunctional HDL having pathological activity acting on arteriosclerosis rather increases in patients with coronary artery disease. The present inventors have found that the total amount of blood adiponectin also includes an adiponectin having physiological activity and an adiponectin having pathological activity, as in the case of HDL, and that when the concentration of adiponectin having pathological activity is high, the physiological activity cannot be exhibited.

Taking these findings into consideration, the present inventors considered that it was necessary to accurately measure the physiological activity of adiponectin, and proceeded with intensive research.

The present invention has been made in view of the circumstances as described above, and the objective thereof is to provide a method for quantifying adiponectin that can accurately understand the physiological activity of adiponectin and is useful for evaluating the risk of cardiovascular disease, lifestyle-related disease, and the like, and also provide an analytical reagent used for the quantification method thereof.

Solution to Problem

In order to solve the above problems, the present invention includes the following aspects.

[1] A method for quantifying adiponectin, comprising quantifying adiponectin while distinguishing between an adiponectin having physiological activity and an adiponectin having pathological activity in a quantification of adiponectin in body fluid.

[2] The method for quantifying adiponectin according to [1], wherein in the quantification of adiponectin in body fluid, a T-cadherin protein is used for quantification of adiponectin having physiological activity.

[3] The method for quantifying adiponectin according to [1], wherein in the quantification of adiponectin in body fluid, the T-cadherin protein is a recombinant T-cadherin protein.

[4] The method for quantifying adiponectin according to any one of [1] to [3], wherein in the quantification of adiponectin in body fluid, the quantification of adiponectin having physiological activity is performed by immunoassay of a complex of an adiponectin, a T-cadherin protein and an anti-adiponectin antibody.

[5] The method for quantifying adiponectin according to any one of [1] to [4], wherein in the quantification of adiponectin in body fluid, the quantification of adiponectin having pathological activity is performed using a conjugate of an adiponectin and a modified low-density lipoprotein.

[6] The method for quantifying adiponectin according to any one of [1] to [5], wherein in the quantification of adiponectin in body fluid, a LOX-1 protein is used for the quantification of adiponectin having pathological activity.

[7] The method for quantifying adiponectin according to [6, wherein in the quantification of adiponectin in body fluid, the LOX-1 protein is a recombinant LOX-1 protein.

[8] The method for quantifying adiponectin according to [7, wherein in the quantification of adiponectin in body fluid, the quantification of adiponectin having pathological activity is performed by quantifying receptor-binding activity by immunoassay using the recombinant LOX-1 protein.

[9] The method for quantifying adiponectin according to [8, wherein in the quantification of adiponectin in body fluid, the quantification of adiponectin having pathological activity is performed by quantifying receptor-binding activity of a complex of an anti-adiponectin antibody, an adiponectin and a modified low-density lipoprotein using the recombinant LOX-1 protein.

[10] The method for quantifying adiponectin according to any one of [1] to [9], wherein in the quantification of adiponectin in body fluid,
a T-cadherin protein is used in the quantification of adiponectin having physiological activity, a recombinant LOX-1 protein is used for the quantification of adiponectin having pathological activity, and
receptor-binding activity is quantified by immunoassay.

[11] The method for quantifying adiponectin according to any one of [1] to [10], wherein in the quantification of adiponectin in body fluid,
a T-cadherin protein is used for the quantification of adiponectin having physiological activity,
a conjugate of adiponectin and modified low-density lipoprotein, and a recombinant LOX-1 protein are used for the quantification of adiponectin having pathological activity, and
receptor-binding activity is quantified by anti-adiponectin immunoassay.

[12] The method for quantifying adiponectin according to any one of [1] to [11], wherein in the quantification of adiponectin in body fluid, the body fluid is blood or saliva.

[13] An analytical reagent used for quantifying adiponectin in body fluid for determining cardiovascular disease, diabetes or diabetic disease, or the progress thereof, comprising
a recombinant T-cadherin protein for quantification of adiponectin having physiological activity.

[14] An analytical reagent used for quantifying adiponectin in body fluid for determining cardiovascular disease, diabetes or diabetic disease, or the progress thereof, comprising
a recombinant LOX-1 protein for quantification of adiponectin having pathological activity, wherein
receptor-binding activity is quantified by immunoassay of anti-adiponectin for a complex of an adiponectin and a modified low-density lipoprotein.

Advantageous Effects of Invention

According to the present invention, a method for quantifying adiponectin that can accurately understand the physiological activity of adiponectin and is useful for evaluating the risk of cardiovascular disease, lifestyle-related disease, and the like, can be obtained, and also an analytical reagent used for the quantification method thereof can be obtained.

DESCRIPTION OF EMBODIMENTS

Figure 1:
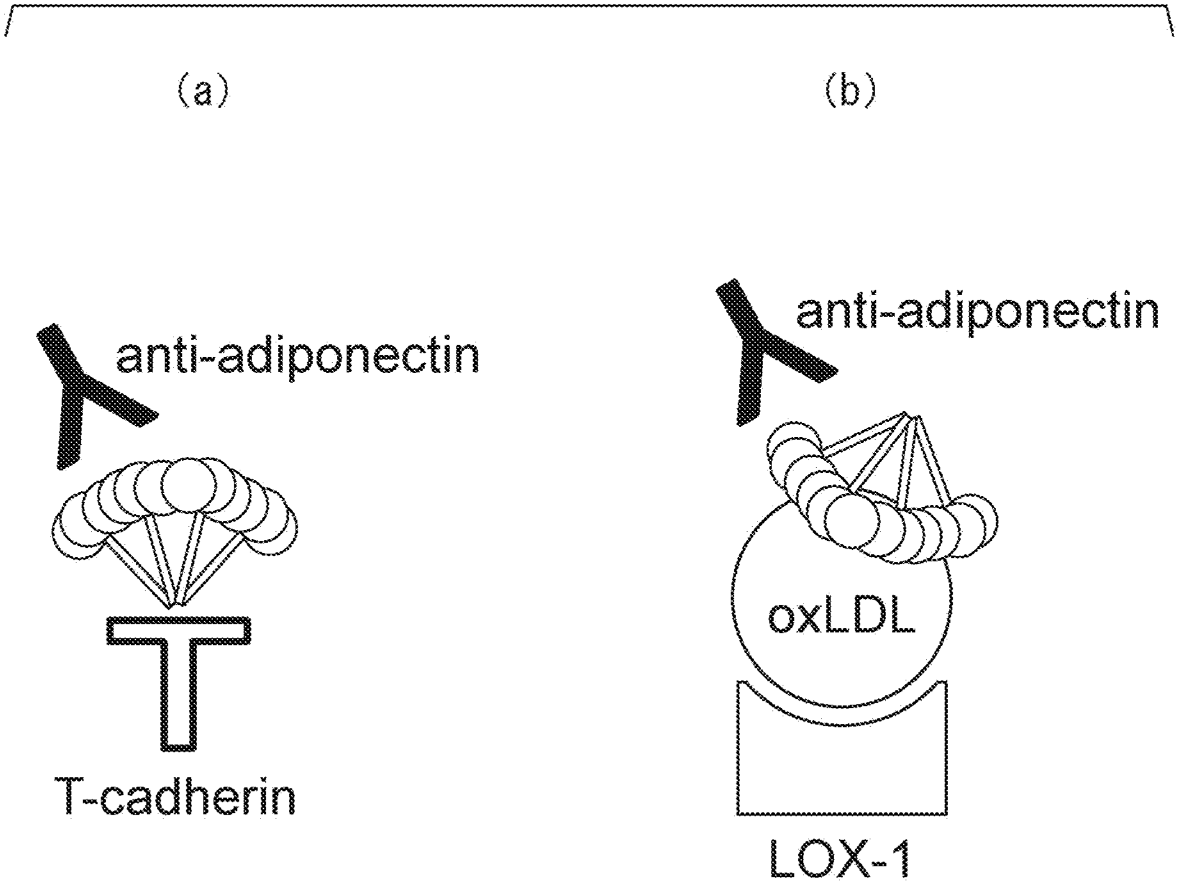
FIG. 1 is a schematic diagram showing an outline of the method for quantifying adiponectin used in the Examples of the present invention.

Hereinafter, the method for quantifying adiponectin and the reagent for analysis according to the present invention will be described with reference to embodiments. However, the present invention is not limited to the following embodiments.

(Method for Quantifying Adiponectin)

In the method for quantifying adiponectin of the present embodiment, adiponectin in body fluid is quantified while distinguishing between an adiponectin having physiological activity and an adiponectin having pathological activity.

Here, the adiponectin having physiological activity refers to, for example, adiponectin capable of binding to an adiponectin receptor and exerting a physiological action via the adiponectin receptor. Examples of adiponectin receptors include AdipoR1, AdipoR2, and T-cadherin.

The adiponectin having physiological activity may also be referred to as a functional adiponectin.

The adiponectin having pathological activity refers to adiponectin that is less likely to exhibit the original physiological activity of adiponectin, and examples thereof include those that have lost their physiological activity, those whose physiological activity is greatly reduced, those that have acquired non-physiological activity, and the like. Such adiponectins are, for example, adiponectins with reduced responses mediated by adiponectin receptors.

For example, mechanisms by which an adiponectin having physiological activity loses physiological activity include factors such as chemical modification or partial or complete degradation of constituent proteins, genetic defects and mutations, abnormalities or changes in higher-order structure, or binding to molecules that cause it to lose its activity.

Adiponectin having pathological activity interacts with receptors that cause adverse reactions in the body, such as LOX-1 (Lectin-like oxygenated LDL receptor-1), and has acquired the ability to bind to LOX-1, including those mediated by other proteins. In the present embodiment, although adiponectin that is less likely to exhibit physiological activity is referred to as an adiponectin having pathological activity, taking the acquisition of such binding ability as an example, the activities of adiponectin having pathological activity are not limited to the above.

In addition, the adiponectin having pathological activity may also be referred to as dysfunctional adiponectin.

Quantifying adiponectin while distinguishing between an adiponectin having physiological activity and an adiponectin having pathological activity includes, for example, a means capable of quantifying only the adiponectin having physiological activity, a means capable of quantifying only the adiponectin having pathological activity, or a quantification of each using these means in combination. In addition, it also includes a means of distinguishing and separating the adiponectin having physiological activity from the adiponectin having pathological activity to quantify each of them.

In the present embodiment, either the adiponectin having physiological activity or the adiponectin having pathological activity can be quantified. On the other hand, it is also preferable to quantify both the adiponectin having physiological activity and the adiponectin having pathological activity. By analyzing these results together and using them for evaluation, the risk of disease and the like can be determined more accurately.

Known means for quantification of protein (measurement of protein amount) can be used for the above quantification. For example, immunological techniques can be used for the above quantification.

Enzymes (enzyme immunoassay, EIA, ELISA), fluorescent substances (fluorescence immunoassay, FIA), radioactive substances (radioimmunoassay, RIA), etc. can be appropriately used for the quantification and the immunoassay using immunological techniques. Among these, ELISA is preferable because it is relatively inexpensive, simple, and can analyze a large number of samples.

For example, in the present embodiment, the ELISA method can be used for the quantification. Specifically, a compound that can bind to a subject to be quantified is immobilized on an ELISA plate. A sample is added to the ELISA plate to allow the subject to be quantified and contained in the sample to bind to the receptor, the plate is washed to remove unbound material, and detected with an antibody to the subject to be quantified, thereby quantifying the conjugate between the subject to be quantified and the compound capable of binding to the subject.

In the present embodiment, receptors for physiological action are used as the compound capable of binding to the subject to be quantified. In the present embodiment, a receptor capable of binding only to the adiponectin having physiological activity and a receptor capable of binding only to the adiponectin having pathological activity are used. Further, hereinafter, the activity of each adiponectin to bind to the receptor may be referred to as receptor binding activity. In other words, the quantification of each adiponectin in the present embodiment is the quantification of the receptor binding activity to each receptor.

Known methods can be appropriately used for immobilization of the receptor. For example, the receptor can be bound to a known carrier (support).

In the present embodiment, adiponectin contained in the body fluid will be quantified. Here, for example, blood or saliva can be used as the body fluid. Serum, plasma, or the like can be used as the blood sample. In the present embodiment, these body fluids are used as samples and subjected to the above-described quantification.

Although the body fluid samples described above preferably do not contain EDTA, samples such as plasma may contain EDTA, which is a calcium ion inhibitor, for preservation. However, the binding of T-cadherin and adiponectin has been reported to be calcium dependent. Therefore, when the sample does not contain EDTA, which is a calcium ion inhibitor, the above-described quantification method can be preferably used.

(Quantification of Adiponectin Having Physiological Activity)

When quantifying adiponectin in body fluid, T-cadherin proteins are preferably used for quantifying the adiponectin having physiological activity. Examples of the T-cadherin proteins of the present embodiment include known families of T-cadherin proteins, modified proteins, and the like.

A T-cadherin protein is one of the receptors of adiponectin having physiological activity. By quantifying the adiponectin interacting (for example, binding) with the T-cadherin protein, the adiponectin having physiological activity can be quantified while distinguishing it from the adiponectin having pathological activity.

In quantifying adiponectin in body fluid, as the T-cadherin protein, recombinant T-cadherin proteins can also be preferably used. Here, the recombinant T-cadherin protein is a T-cadherin protein obtained by expression through gene recombination. The recombinant T-cadherin protein may be fused with other structures or mutated, if necessary.

In quantifying adiponectin in body fluid, it is also preferable to quantify the adiponectin having physiological activity by immunoassay of a complex of an adiponectin, a T-cadherin protein and an anti-adiponectin antibody.

Specifically, a conjugate of adiponectin and a T-cadherin protein can be bound to an anti-adiponectin antibody, and the conjugate can be quantified by immunoassay. For example, the T-cadherin protein is immobilized on an ELISA plate. By injecting a reagent derived from body fluid onto this ELISA plate, the adiponectin having physiological activity is allowed to bind to the T-cadherin protein on the ELISA plate. This conjugate on the ELISA plate can be quantified with an anti-adiponectin antibody.

Both monoclonal and polyclonal antibodies can be used as the anti-adiponectin antibody in the present embodiment.

(Quantification of Adiponectin Having Pathological Activity)

In quantifying adiponectin in body fluid, it is preferable to quantify the adiponectin having pathological activity using a conjugate of an adiponectin and a modified low-density lipoprotein.

The modified low-density lipoprotein (hereinafter also referred to as modified LDL) is an LDL (Low-Density Lipoprotein) protein that has been modified for a specific reason. Here, the LDL is commonly known as bad cholesterol, and is known to be responsible for transporting cholesterol from the liver to the periphery. Examples of the modified LDL include an oxidized LDL (OxLDL) or the like.

According to the present inventors, there are verification results showing that adiponectin is concentrated in the modified low-density lipoprotein fraction, and showing that the oxidized LDL, which is a modified LDL, inhibits the action of adiponectin.

Figure 8:
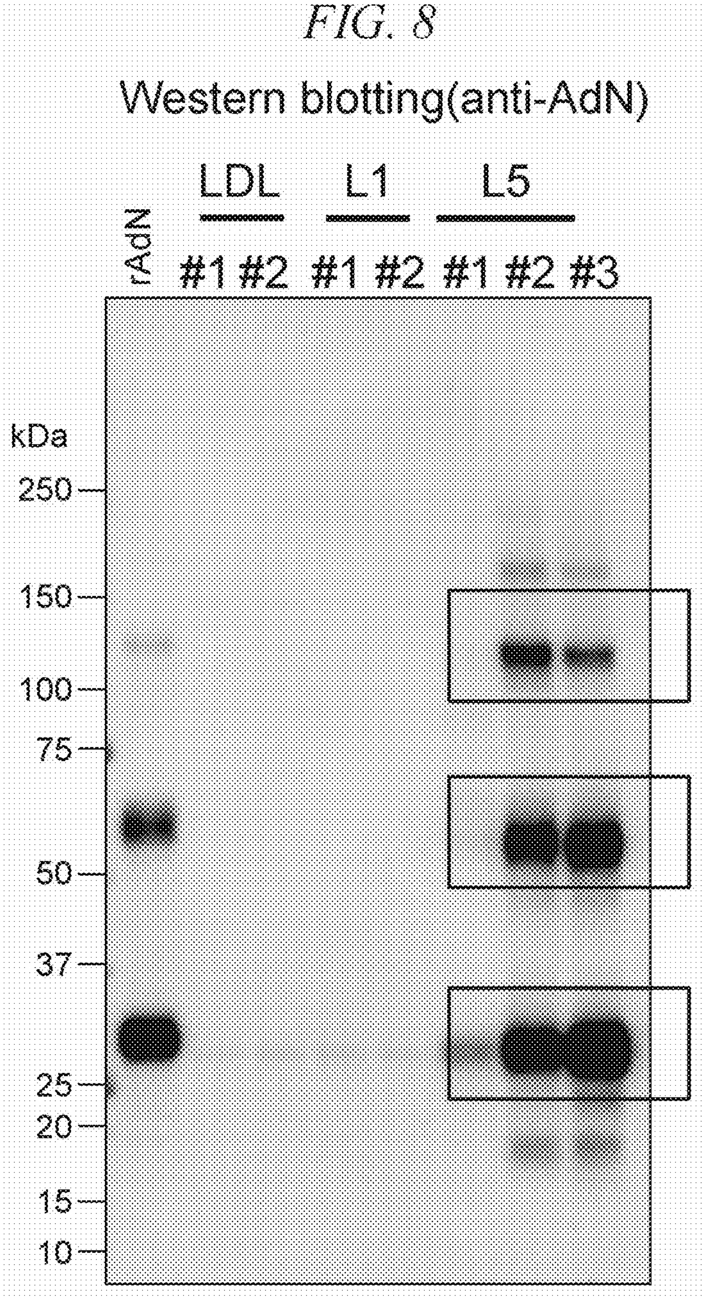
FIG. 8 shows the binding test between modified LDL and adiponectin in a reference test of the present application.
Figure 9:
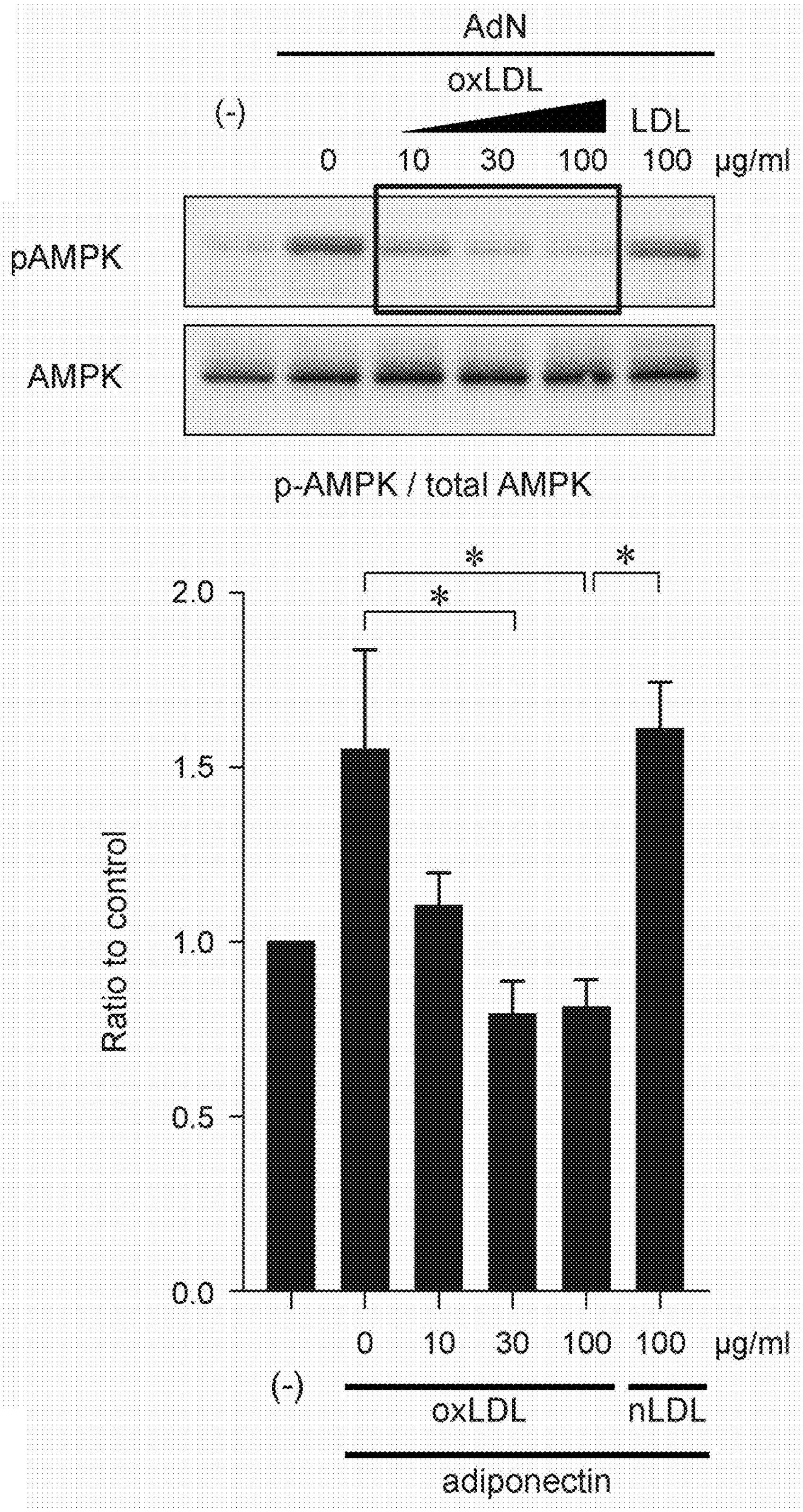
FIG. 9 shows a test in which AMPK and its phosphorylation (pAMPK) were detected with an anti-adiponectin antibody.

According to the studies by the present inventors, as shown in FIG. 8 to be described later, in human blood, adiponectin is concentrated in the fraction corresponding to the modified LDL, and interaction between the adiponectin and the modified LDL occurs in vivo. As shown in FIG. 9 to be described later, the modified LDL has an effect of inhibiting AMPK (AMP kinase) phosphorylation of adiponectin. In the presence of modified LDL, adiponectin is considered to bind to the modified LDL and lose its original AdipoR1-mediated action. Therefore, it was expected that the interaction between the modified LDL and the adiponectin would cause the adiponectin to exhibit pathological activity.

From these results, the present inventors found that the modified low-density lipoprotein interacts with the adiponectin to lose its physiological activity, and that the modified low-density lipoprotein can be used to quantify the adiponectin having pathological activity.

In the quantification of adiponectin having pathological activity, for quantification using a conjugate of an adiponectin and a modified low-density lipoprotein, for example, a protein that specifically binds to the modified low-density lipoprotein and an anti-adiponectin antibody can be used to detect and quantify the conjugate of an adiponectin and a modified low-density lipoprotein.

By quantifying the adiponectin interacting with (for example, binding to) the modified low-density lipoprotein, the adiponectin having pathological activity can be quantified while distinguishing it from the adiponectin having physiological activity.

In quantifying adiponectin in body fluid, it is also preferable to use a protein that interacts with the modified low-density lipoprotein for quantifying the adiponectin having pathological activity. As the protein that interacts with the modified low-density lipoprotein, for example, a LOX-1 protein is also preferable. The LOX-1 is a molecule discovered by the present inventors (Sawamura T et al. Nature 386, 73-77, 1997) and is known as a lectin-like oxidized LDL receptor. The detailed structure of the LOX-1 has also been clarified, and it is known that the LOX-1 is a single-pass membrane protein and has a lectin-like domain, and this lectin-like domain is a recognition site for the oxidized LDL (JP-A-9-98787, etc.), and also that a soluble component is present in the blood, and the modified high-density lipoprotein (HDL) acts as a ligand for the LOX-1 (JP-A-2012-100585, JP-A-6231307, etc.).

In the quantification of adiponectin in body fluid, as the LOX-1 protein, a recombinant LOX-1 protein can also be preferably used. Here, the recombinant LOX-1 protein is a LOX-1 protein obtained by expression through genetic recombination. The recombinant LOX-1 protein may be fused with other structures or mutated, if necessary.

In the quantification of adiponectin in body fluid, it is also preferable to quantify the adiponectin having pathological activity by immunoassay of the receptor-binding activity using the recombinant LOX-1 protein.

This quantification is also preferably carried out by quantifying the receptor-binding activity by immunoassay of a complex of an anti-adiponectin antibody, an adiponectin and a modified low-density lipoprotein.

Specifically, a conjugate of an adiponectin and a modified low-density lipoprotein is allowed to bind to an anti-adiponectin antibody, and the resulting complex can be quantified by immunoassay.

In the immunoassay described above, as means for quantifying the complex of the recombinant LOX-1 protein, a modified low-density lipoprotein and an adiponectin can be used. This quantification can be carried out using a so-called sandwich ELISA. For this quantification method, for example, a LOX-1, which is a low-density lipoprotein receptor, is immobilized on an ELISA plate, and a modified low-density lipoprotein is allowed to bind to the LOX-1 on the ELISA plate. By injecting a reagent derived from a body fluid into this ELISA plate, the complex of the LOX-1 and a modified low-density lipoprotein is allowed to bind to the adiponectin having pathological activity. Then, the conjugate on the ELISA plate can be quantified with an anti-adiponectin antibody.

In the quantification of adiponectin in body fluid, the quantification of adiponectin having physiological activity and the quantification of adiponectin having pathological activity can be used in combination. For example, it is possible to use a T-cadherin protein to quantify the adiponectin having physiological activity, and use a conjugate of an adiponectin and a modified low-density lipoprotein, and a recombinant LOX-1 protein to quantify the receptor-binding activity by immunoassay of anti-adiponectin, thereby quantifying the adiponectin having pathological activity.

(Analytical Reagent Used for Quantification of Adiponectin)

Next, the analytical reagent used in the above-described method for quantifying adiponectin in body fluid will be described.

This analytical reagent can be used to quantify adiponectin in body fluids to determine cardiovascular disease, diabetes or diabetic disease, or the degree of progression thereof.

The analytical reagent contains the recombinant T-cadherin protein described above. By containing the recombinant T-cadherin protein, it is possible to quantify the adiponectin having physiological activity.

In addition, the analytical reagent may also contain the recombinant LOX-1 protein for quantification of adiponectin having pathological activity.

As described above, since the recombinant LOX-1 protein interacts with the modified low-density lipoprotein in this analytical reagent, the adiponectin having pathological activity can be quantified by quantifying the receptor-binding activity of the conjugate of an adiponectin and a modified low-density lipoprotein by anti-adiponectin immunoassay.

(Other Configurations)

The analytical reagent of the present embodiment may contain other components that may be contained in immunological analysis reagents.

Moreover, the analytical reagent of the present embodiment may be provided as a kit including a plurality of the above-described configurations. For example, the kit may include an analytical reagent containing a recombinant T-cadherin protein for quantifying the adiponectin having physiological activity and an analytical reagent containing a recombinant LOX-1 protein for quantifying the adiponectin having pathological activity. The kit may also include a recombinant low-density lipoprotein for quantification of adiponectin having pathological activity. Further, the kit may also include a carrier, an ELISA plate, a chromogenic substrate, an antibody or the like for use in the above-described quantification procedure. Further, an ELISA plate on which the above-described proteins are immobilized may also be included.

Effect of the Present Embodiment

According to the method for quantifying adiponectin and the analytical reagent of the present embodiment, the physiological activity of adiponectin can be accurately understood, and it can be used to evaluate cardiovascular disease risk, lifestyle disease risk, and the like.

The quantification method and the analytical reagent of the present embodiment are highly likely to be useful for stratifying cardiovascular disease risk by quantifying the adiponectin while distinguishing between the adiponectin having physiological activity and the adiponectin having pathological activity. Moreover, it is highly possible that the quantification method and the analytical reagent can be applied to arteriosclerotic diseases, particularly coronary artery diseases, diabetes, and diabetic diseases. These diseases include many so-called lifestyle-related diseases. Therefore, all people aged 40 and over, who are at increased risk of lifestyle-related diseases, are subject to disease risk assessment, prevention, and diagnosis, and the social scope of the application is extremely wide.

The quantification method of the present embodiment can be applied to in-vitro diagnosis for predicting cardiovascular disease risk. Since the quantification method of the present embodiment is mainly intended for cardiovascular disease risk assessment, it can be used for secondary risk assessment for patients who have already had adverse cardiovascular events and for primary risk assessment for healthy subjects. In addition, the analytical reagent of the present embodiment and the kit including the same can be applied as an agent for these in-vitro diagnostics.

Application of the Present Embodiment

The method for quantifying adiponectin and the analytical reagent of the present embodiment can be used, for example, for a method for diagnosing cardiovascular disease and/or diabetes or diabetic disease by measuring the adiponectin having physiological activity in the quantification of adiponectin in body fluid.

In addition, it can be suitably used for a method for diagnosing the above-described cardiovascular diseases, such as arteriosclerotic disease, coronary artery disease or the like.

In the diagnostic method, it is also possible to diagnose the risk of cardiovascular diseases, diabetes and diabetic diseases, and/or the progression degree of these diseases based on the change in the ratio of adiponectin having pathological activity to adiponectin having physiological activity, and the change in the ratio of adiponectin having physiological activity to the total adiponectin, which is a sum of the amount of adiponectin having physiological activity and the amount of adiponectin having pathological activity obtained by measuring the adiponectin having physiological activity in the quantification of adiponectin in the body fluid.

This diagnostic method also includes a process in which protein standards, healthy body fluid samples, etc. are used as standard products to prepare a calibration curve, a comparison table and the like, and the quantitative results of the specimen sample to be diagnosed are compared with the calibration curve and the comparison table to make a diagnosis.

In addition, it can be used for determining and diagnosing obesity-related diseases such as hypertension, sleep apnea, risk thereof, and/or the progression degree thereof.

EXAMPLES

Examples are shown below. In addition, the present invention is not limited to the examples.

(Summary of Quantification Method for Adiponectin)

The outline of the method for quantifying adiponectin used in the Examples is shown below.

FIG. 1(*a*) shows a schematic diagram of the detection of adiponectin having physiological activity. An adiponectin having physiological activity is bound to a T-cadherin capable of interacting with the adiponectin. The adiponectin site of the conjugate of the adiponectin having physiological activity and the T-cadherin is quantified by immunoassay with an anti-adiponectin.

FIG. 1(*b*) shows a schematic diagram of the detection of adiponectin having pathological activity. An adiponectin having pathological activity is bound to a modified low-density lipoprotein (OxLDL) capable of interacting with the adiponectin. Furthermore, a LOX-1 protein capable of interacting with the modified low-density lipoprotein is bound to the modified low-density lipoprotein. The adiponectin sites of the complex of the adiponectin having pathological activity, the modified low-density lipoprotein and the LOX-1 protein are quantified by immunoassay with an anti-adiponectin.

(Quantification of Adiponectin Having Physiological Activity)

First, the binding of the adiponectin having physiological activity and the T-cadherin was tested.

A human T-cadherin gene was cloned, inserted into pSeqTag2 vector (Invitrogen), and used in a protein expression system. Protein expression was performed using Expi293 Expression System (Invitrogen), and the fusion protein secreted into the medium was His-purified using Ni Sepharose excel resin (GE). The obtained protein was dialyzed in PBS and used for the experiment after filter filtration sterilization.

The purified T-cadherin protein was immobilized on an ELISA plate, bound with the adiponectin recombinant protein, and the bound adiponectin was detected with an anti-adiponectin antibody.

Figure 2:
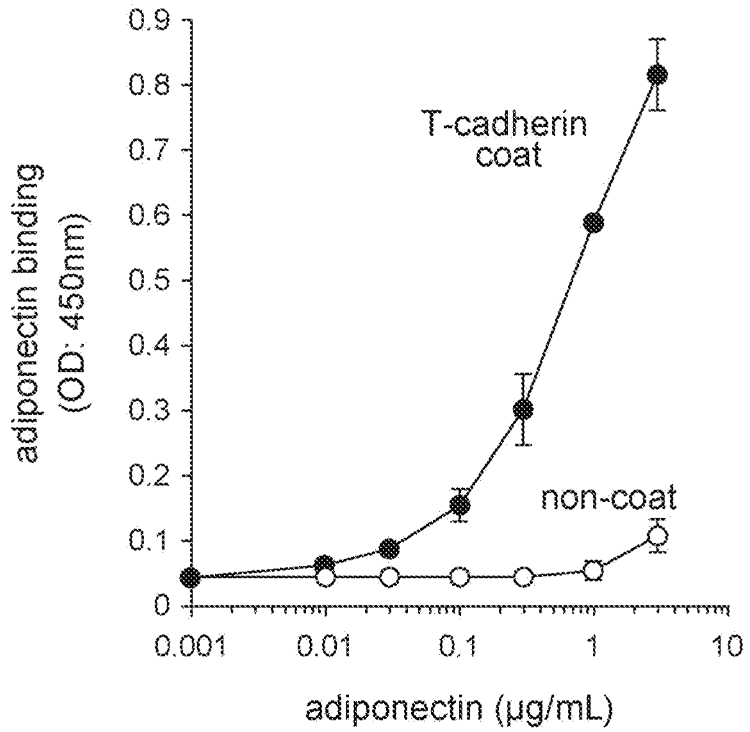
FIG. 2 is a graph showing the results of a binding test between an adiponectin having physiological activity and a T-cadherin.

The results are shown in FIG. 2. As for the T-cadherin-immobilized ELISA plate, the binding amount increases depending on the concentration of the added adiponectin. That is, it was demonstrated that the concentration of adiponectin having physiological activity and binding to the T-cadherin in a sample, can be quantified using a T-cadherin-immobilized plate.

Then, the concentration of adiponectin having physiological activity in a human serum sample was quantified. Immobilization on an ELISA plate and detection were performed under the following conditions.

Immobilization: T-cadherin protein (139-692aa), 0.15 μg/well

Blocking: 1% casein-Na, in HEPES-NaCl, 2 hours, room temperature

Figure 3:
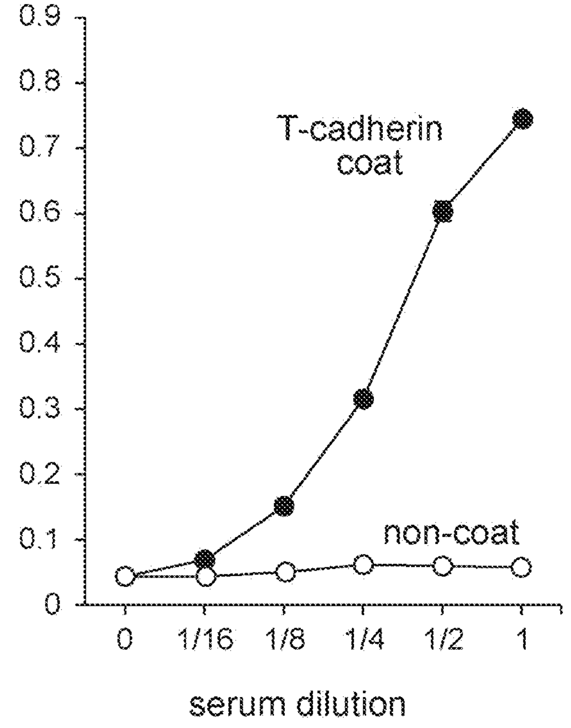
FIG. 3 is a graph showing the results of a quantitative test of concentration of adiponectin having physiological activity in human serum samples.

Ligand: adiponectin, in HEPES-NaCl, 2 hours, room temperature, serum, in HEPES-NaCl Detection: primary antibody, anti-adiponectin antibody (rabbit polyclonal; BioVendor #RD181023100), 1 μg/ml, in 1% casein-Na/HEPES-NaCl, 1 hour, room temperature secondary antibody, anti-rabbit IgG-HRP, 1:4000, in 1% casein-Na/HEPES-NaCl, 1 hour, room temperature The results are shown in FIG. 3. It was shown that the binding amount increases according to the concentration of serum, namely the concentration of adiponectin, in the sample, and that the concentration of adiponectin having physiological activity can be quantified.

Figure 4:
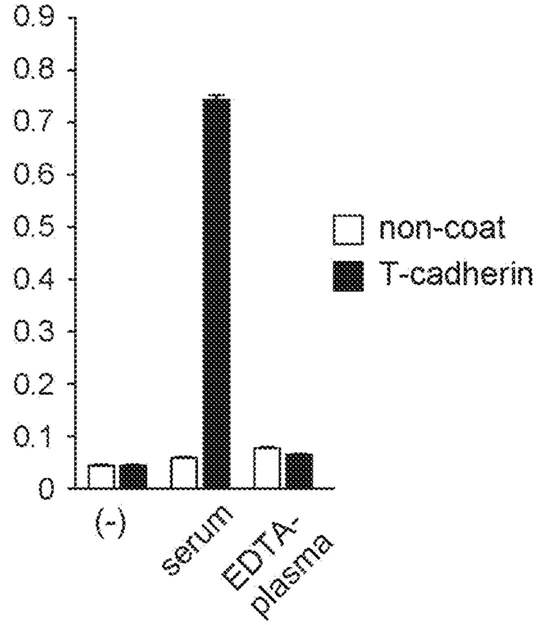
FIG. 4 is a graph showing the results of a quantitative test of concentration of adiponectin having physiological activity in a human serum sample and a plasma sample containing EDTA.

On the other hand, a quantification was also performed under the same conditions as described above except that a plasma containing EDTA was used as a sample. FIG. 4 shows a comparison of binding amounts between serum and plasma (EDTA-Plasma). The binding amount was reduced in the plasma containing EDTA. This is because, as previously reported, the binding of the T-cadherin and the adiponectin is calcium dependent (Hug C, Proceedings of the National Academy of Sciences of the United States of America, 2004). Since the binding was inhibited in the plasma in the presence of EDTA, which is a calcium inhibitor, it was shown that the conventionally known binding of T-cadherin and adiponectin occurs in the serum.

Based on these results, it is possible to detect and quantify the adiponectin having physiological activity in a blood sample that binds to a T-cadherin using ELISA.

(Quantification of Adiponectin Having Pathological Activity)

The binding of the adiponectin having pathological activity to the modified LDL was then tested.

LDL isolated from the human plasma was oxidized in vitro in the presence of copper ions to obtain an oxidized LDL, which is a modified LDL. This oxidized LDL and a recombinant adiponectin protein were mixed, and it was examined whether the complex of the two could be detected by the sandwich ELISA of modified LDL receptor LOX-1 and an anti-adiponectin antibody. As the LOX-1, a recombinant LOX-1 obtained by expressing a human LOX-1 in the same protein expression system as described above and purifying it was used.

Figure 5:
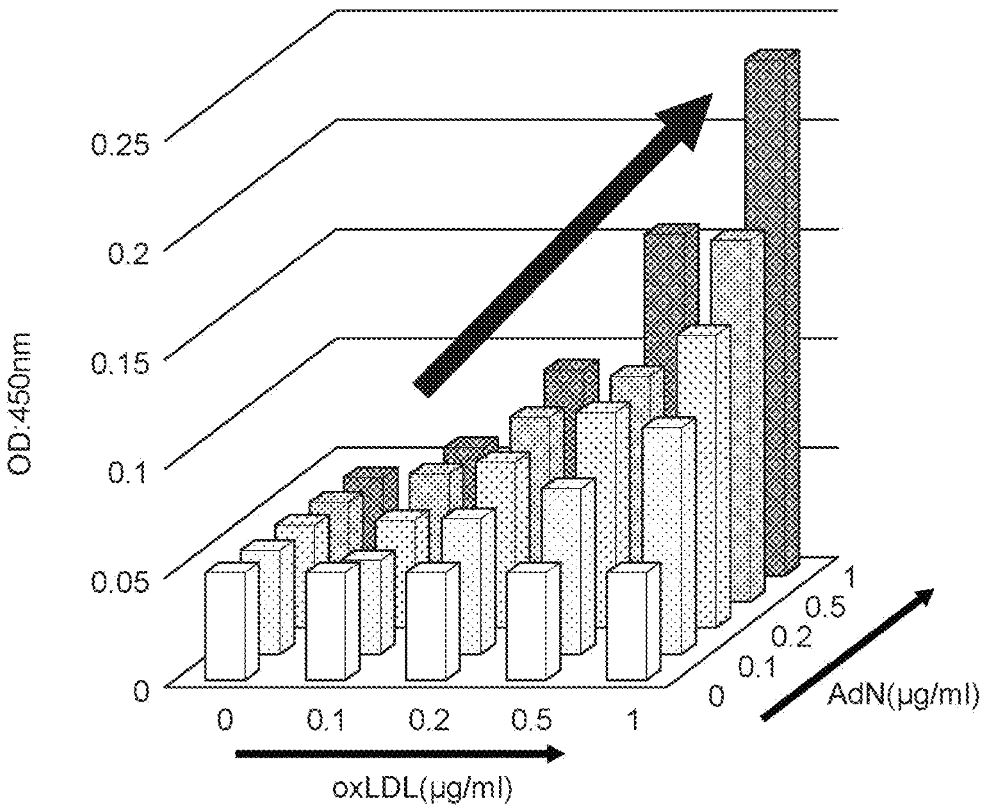
FIG. 5 is a graph showing the results of a binding test between an adiponectin having pathological activity and a modified LDL.

FIG. 5 shows the quantifying results of the mixed solution of the purified adiponectin and the oxidized LDL using an anti-adiponectin antibody. As shown in the results, not only the purified adiponectin (AdN) concentration, but also the detection of purified adiponectin was increased depending on the concentration of oxidized LDL (oxLDL). This indicates that a complex of oxidized LDL and an adiponectin can be detected by ELISA.

Quantification of the concentration of adiponectin having pathological activity in a human serum sample was then performed. A healthy serum and an arteriosclerosis patient's blood were purchased from a supplier and used as a serum sample.

Immobilization on an ELISA plate and detection were performed under the following conditions.

Immobilization: LOX-1, 0.15 μg/well

Blocking: 1% casein-Na, in HEPES-NaCl, 2 hours, room temperature

Figure 6:
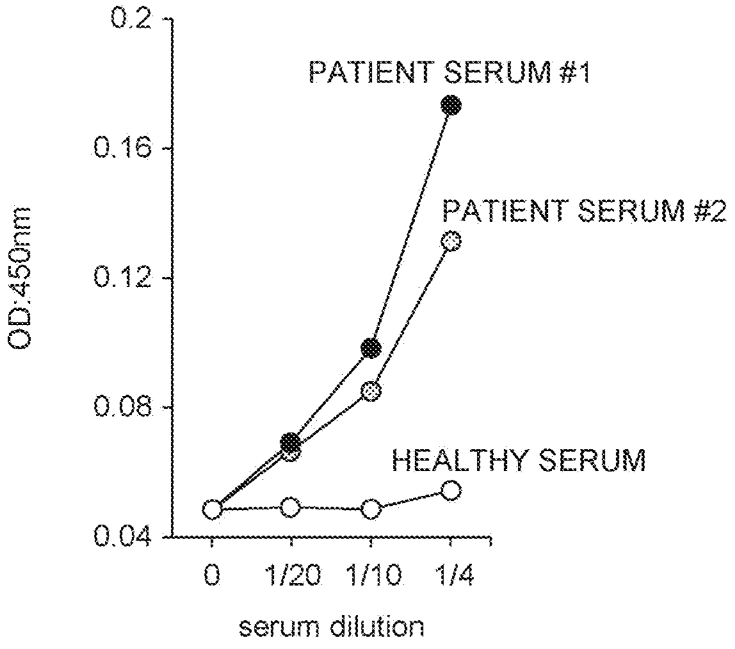
FIG. 6 is a graph showing the results of a quantitative test of concentration of adiponectin having pathological activity in human serum samples.

Ligand: oxidized LDL, adiponectin complex, in HEPES-NaCl-2 mM EDTA, 2 hours, room temperature Detection: primary antibody, anti-adiponectin antibody (rabbit polyclonal) 1 μg/ml, in 1% casein-Na/HEPES-NaCl, 1 hour, room temperature secondary antibody anti-rabbit IgG-HRP, 1:4000, in 1% casein-Na/HEPES-NaCl, 1 hour, room temperature The results are shown in FIG. 6. As shown in the results, compared to the healthy serum, in the patient with arteriosclerotic disease, the quantification by an anti-adiponectin antibody, namely, the complex of the LOX1, the oxidized LDL and the adiponectin having pathological activity showed a higher value.

Figure 7:
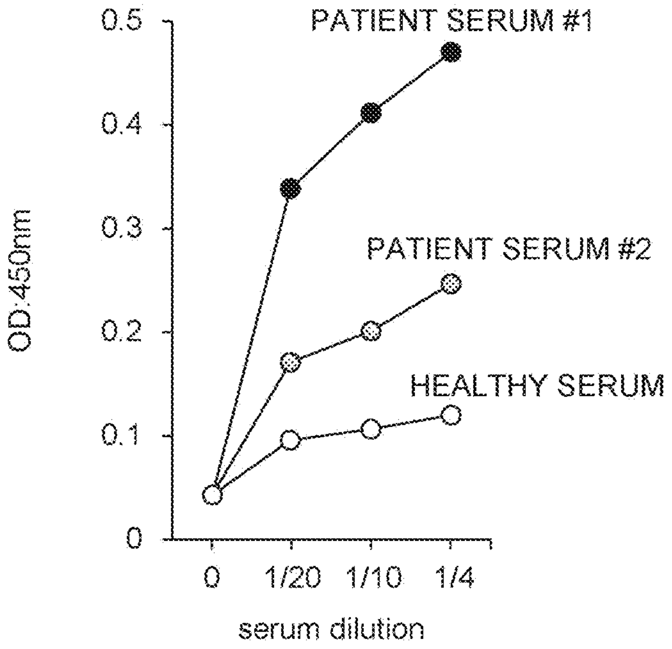
FIG. 7 is a graph showing the results of a quantitative test of concentration of LOX-1-binding modified LDL in human serum samples.

FIG. 7 shows the results of detection of a LOX-1-binding modified LDL using the HUC20 antibody as the detection antibody. As in the case of FIG. 6, the patient with arteriosclerotic disease showed a higher value than the healthy serum. The patients with patient serum #1 showing a high value in the results of FIGS. 6 and 7 are predicted to have more advanced arteriosclerotic disease than the patients with patient serum #2.

These results indicate that this test can determine arteriosclerotic disease or its progression.

(Reference Test)

FIG. 8 shows the results of detection of the LDL fractionated from human plasma with an anti-adiponectin antibody. Among the LDL fractions, the subfraction L5 indicates an electronegative LDL and corresponds to a modified LDL. As shown in the figure, adiponectin was enriched in the subfraction L5. That is, it indicates the possibility that a modified LDL and an adiponectin are bound.

FIG. 9(*a*) shows the results of detection of AMPK and its phosphorylation (pAMPK) using an anti-adiponectin antibody, and FIG. 9(*b*) shows the detected amount. As shown in the results, the detected amount of the anti-adiponectin antibody of pAMPK decreased in an oxLDL concentration-dependent manner, indicating the possibility that the oxidized LDL inhibits AMPK phosphorylation by adiponectin. This result indicates the possibility that the oxidized LDL acts on adiponectin, and inhibits the action of adiponectin, thereby converting an adiponectin having physiological activity to an adiponectin having pathological activity.

INDUSTRIAL APPLICABILITY

According to the present invention, a method for quantifying adiponectin that can accurately understand the physiological activity of adiponectin and is useful for evaluating the risk of cardiovascular disease, lifestyle-related disease, and the like, can be obtained, and also an analytical reagent used for the quantification method thereof can be obtained. This quantification method and analytical reagent can be used, in particular, to determine the risk or progression of cardiovascular disease, diabetes, and diabetes.

The invention claimed is:

1. A method for quantifying adiponectin in a body fluid comprising:

(a) measuring by immunoassay a complex comprising adiponectin, a T-cadherin protein, and an anti-adiponectin antibody to quantify adiponectin having physiological activity; and (b) measuring by immunoassay receptor-binding activity of a complex comprising an anti-adiponectin antibody, adiponectin, and a modified low-density lipoprotein using a LOX-1 protein to quantify adiponectin having pathological activity.

2. The method for quantifying adiponectin according to claim 1, wherein in the measuring of adiponectin in body fluid, the T-cadherin protein is a recombinant T-cadherin protein.

3. The method for quantifying adiponectin according to claim 1, wherein in the measuring of adiponectin in body fluid, the LOX-1 protein is a recombinant LOX-1 protein.

4. The method for quantifying adiponectin according to claim 1, wherein in the measuring of adiponectin in body fluid, the body fluid is blood or saliva.

* * * * *